United States Patent [19]

Aida et al.

[11] 4,220,719
[45] Sep. 2, 1980

[54] PROCESS FOR THE PRODUCTION OF COENZYME $Q_{10}$

[75] Inventors: Kô Aida, No. 681-2, Oazanegishi, Urawa-shi, Saitama-ken, Japan; Kinya Uchida, Mitaka, Japan; Izumi Kawada, Yokohama, Japan; Hideichi Ito, Kokubunji, Japan

[73] Assignee: Ko Aida, Urawa, Japan

[21] Appl. No.: 18,114

[22] Filed: Mar. 7, 1979

[30] Foreign Application Priority Data

Mar. 20, 1978 [JP] Japan ................................. 53-31098

[51] Int. Cl.$^3$ ............................................... C12P 7/66
[52] U.S. Cl. ................................... 435/133; 435/916; 435/944; 435/911
[58] Field of Search ........................................ 435/133

[56] References Cited

U.S. PATENT DOCUMENTS 4,070,244  1/1978  Nakao et al. ..................... 435/133

*Primary Examiner*—Alvin E. Tanenholtz
*Attorney, Agent, or Firm*—Frishauf, Holtz, Goodman & Woodward

[57] ABSTRACT

A process for producing Coenzyme $Q_{10}$ which comprises cultivating a microorganism belonging to genus Cryptococcus, Rhodotorula, Sporobolomyces, Torulopsis, Sporidiobolus, Oosporidium, Aspergillus, and Cladosporium in a culture medium to which isopentenyl alcohol is added and recovering the thus formed Coenzyme $Q_{10}$.

13 Claims, No Drawings

PROCESS FOR THE PRODUCTION OF COENZYME $Q_{10}$

BACKGROUND OF THE INVENTION

1. Field of the invention

The present invention relates to a process for the production of Coenzyme $Q_{10}$. More particularly, it is concerned with a process for the production of Coenzyme $Q_{10}$, which comprises cultivating a microorganism belonging to genus Cryptococcus, Rhodotorula, Sporobolomyces, Torulopsis, Sporidiobolus. Oosporidium, Aspergillus and Cladosporium in a culture medium to which isopentenyl alcohol (3-methyl-3-butene-1-ol) is added to form Coenzyme $Q_{10}$ in the culture medium and recovering the Coenzyme $Q_{10}$ from the microorganisms.

The term "Coenzyme Q" used in the present invention is generally meant 2,3-dimethoxy-5-methyl-1,4-benzoquinones containing an isoprenoid side chain in the 6-position of the quinone nucleus, represented by the general formula:

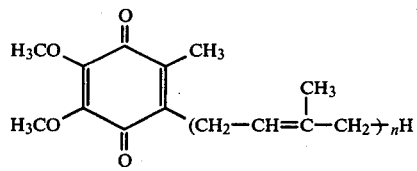

The present invention is intended to provide Coenzyme $Q_{10}$ represented by the above formula in which $n=10$.

Coenzyme Q is widely distributed in animals, plants and microorganisms etc., and it plays an important role as a constituent of the terminal electron transfer system.

2. Explanation of the Prior Art

Recently it has been shown that Coenzyme Q exhibits excellent medical and physiological activities against various diseases. In particular, Coenzyme $Q_{10}$ is considered as the most valuable medicine since Coenzyme Q of human being is Coenzyme $Q_{10}$.

In order to obtain Coenzyme Q, some procedures such as extraction from animal and plant tissues or from microorganisms, and organic synthesis can be employed. It is, however, difficult to produce Coenzyme Q from animal or plant tissue on a large scale. Also it is difficult to produce Coenzyme Q by organic synthesis because of a disadvantage in yields. Thus these procedures are not satisfactory for industrial production. On the other hand, the procedure to extract from microorganisms has the possibility of being employed economically according to the yields of the cells and Coenzyme Q. A comparatively small number of microorganisms have been known to produce Coenzyme $Q_{10}$. Examples of microorganisms which are capable of producing Coenzyme $Q_{10}$ are bacteria such as Pseudomonas denitrificans, Agrobacterium tumefaciens, photosynthetic bacteria such as Rhodospirillum, Rhodomicrobium, Rhodopseudomonas, etc., and some species of yeast and fungi such as Cryptococcus, Rhodotorula, Sporobolomyces, Candida, Torulopsis, Sporidiobolus, Oosporidium, Aspergillus, Cladosporium, etc.

We have investigated to find such compounds that are able to markedly increase the content of Coenzyme $Q_{10}$ per unit cell when these compounds are added to the culture medium for cultivating a microorganism belonging to Cryptococcus, Rhodotorula, Sporobolomyces, Torulopsis, Sporidiobolus, Oosporidium, Aspergillus and Cladosporium, in comparison with the case that they are not added.

Heretofore, p-hydroxy benzoic acid, and acetic acid and its salts are known to be able to increase the content of Coenzyme Q per unit cell when they are added to the culture medium (Japanese Patent Publication No. 20396/1972). It has been known that the isoprenoid side chain of Coenzyme Q is produced through geranyl- and farnesyl pyrophosphate by the biosynthesis in which the condensation reaction of isopentenyl- and dimethyl allyl-pyrophosphate is repeated. However, since it is difficult for these precursors to permeate through the cell membrane, no attempt to make increase the content of Coenzyme Q by adding such precursors to the culture medium have been reported.

SUMMARY OF THE INVENTION

The present invention provides a process for producing Coenzyme $Q_{10}$ which comprises cultivating microorganisms belonging to genus Cryptococcus, Rhodotorula, Sporobolomyces, Torulopsis, Sporidiobolus, Oosporidium, Aspergillus and Cladosporium in a culture medium to which isopentenyl alcohol is added to produce Coenzyme $Q_{10}$ and recovering it.

DETAILED DESCRIPTION OF THE INVENTION

We found that isopentenyl alcohol was utilized by microorganisms capable of producing Coenzyme $Q_{10}$ which belong to genus Cryptococcus, Rhodotorula, Sporobolomyces, Torulopsis, Sporidiobolus, Oosporidium, Aspergillus and Cladosporium in a culture medium to which it is added, and that it was able to markedly increase the content of that it was able to markedly increase the content of Coenzyme $Q_{10}$ per unit cell.

Thus, the present invention is based on this finding and it has been completed after further investigation.

Any of microorganisms belonging to genus Cryptococcus, Rhodotorula, Sporobolomyces, Torulopsis, Sporidiobolus, Oosporidium, Aspergillus and Cladosporium and capable of producing Coenzyme $Q_{10}$ can be employed in the present invention.

The examples of preferential strains of the microorganisms capable of producing Coenzyme $Q_{10}$ in a high yield include *Cryptococcus laurentii* FERM-P4834 (AHU-3926), *Cryptococcus luteolus* IFO-0611, *Rhodotorula, glutinis* FERM-P4835 (AHU-3468), *Rhodotorula flava* IFO-0407, *Rhodotorula peneaus* IRO-0930, *Sporobolomyces salmonicolor* FERM-P4836 (AHU-3982), *Sporobolomyces roseus* IFO-1037, *Sporobolomyces pararoseus* IFO-1103, *Sporobolomyces gracilis* IFO-1033, *Torulopsis aeria* FERM-P4837 (AHU-3397), *Sporidiobolus jonsonii* IFO-6903, *Oosporidium margaritiferum* ATCC-10676, *Aspergillus fumigatus* FERM-P4838 (IAM-2004), *Cladosporium fulvum* FERM-P4839 (IAM-5054) etc.

In the culture medium used in practice of the present invention, sugars such as glucose, molasses etc., and any other carbon sources which these microorganisms are able to utilize, can be used as a carbon source. Inorganic nitrogen compounds such as ammonium sulfate, ammonium chloride and the like, organic nitrogen compounds such as corn steep liquor, extract of fish meat, peptone, yeast extract and the like, can be used as nitrogen sources. In addition, as inorganic salts, potassium salts, sodium salts, magnesium salts, salts of phosphoric acid, sulfuric acid and the like are employed.

The cultivation is usually carried out by agitating with aeration at pH 4 to 7 and temperature of from 25° to 35° C. for 24 to 72 hours.

Isopentenyl alcohol can be added by a desired procedure and at a desired stage of the cultivation. For example, all amounts of the additive are added at the start of the cultivation or at a desired growth stage during the cultivation or they are added little by little according to the state of cultivation. The amount of isopentenyl alcohol to be added is, as a final concentration, usually $1 \times 10^{-5}$ to $5 \times 10^{-3}$ mole/liter, preferably $5 \times 10^{-5}$ to $5 \times 10^{-4}$ mole/liter.

After the cultivation, the Coenzyme $Q_{10}$ which is formed is extracted from the cells and separated from other materials. For example, methanol, sodium hydroxide and pyrogallol are added to the wet cells obtained by centrifuging, and then the mixture is refluxed with heating at 80° to 90° C. for 1 hour to extract Coenzyme $Q_{10}$.

Coenzyme $Q_{10}$ in the extractant is then transferred into a solvent such as petroleum ether and the like, and the fraction containing Coenzyme $Q_{10}$ is subjected to fractional purification by use of alumina column etc., whereby Coenzyme $Q_{10}$ can be isolated.

The identification of Coenzyme $Q_{10}$ can be made by comparing the product of this invention with a standard sample by means of melting point, reversed phase thin layer chromatography using a mixture of acetone:water (95:5) as a solvent, analysis of N.M.R., mass spectrum, etc.

The following examples are given to explain the present invention in more detail, but the present invention is not limited by them.

EXAMPLE 1

In a 30 liter-jar fermentor was placed 15 liters of a culture medium (pH 6.0) containing 0.5% of $KH_2PO_4$, 0.1% of $MgSO_4.7H_2O$, 0.001% of $FeSO_4.7H_2O$, 0.0001% of $ZnSO_4$, 3% of glucose, 0.1% of $(NH_4)_2SO_4$, 0.4% of yeast extract, 0.1% of malt extract. After sterilized with steam, 645 milligrams of isopentenyl alcohol dissolved in 10 milliliters of ethyl alcohol was added. *Cryptococcus laurentii* FERM-P4834, which had been previously cultured in 500 milliliters of the culture medium having the same composition as described above for 36 hours, was inoculated in the above culture medium and cultivated for 48 hours at 30° C. with aeration of 15 liters per minutes under condition of stirring 300 r.p.m. To avoid variation of the pH of the culture medium, aqueous ammonium or aqueous hydrochloric acid was added to maintain the pH 6.0.

After the cultivation, the culture broth was centrifuged whereby 1140 grams of wet cells (143 grams of dry cells) were obtained.

To the wet cells 2.3 liters of methyl alcohol, 550 milliliters of aqueous sodium hydroxide and 114 grams of pyrogallol were added, and saponified by refluxing with heating at 85° C. for 1 hour.

After the saponified solution was cooled, 10 liters of water was added. Thereafter the solution was extracted three times with an equal volume of petroleum ether, and unsaponifiable materials were transferred into the petroleum ether layer. The combined petroleum ether layer was washed with saturated saline solution, dried over anhydrous sodium sulfate and condensed under reduced pressure. The residual oil was dissolved in a small amount of petroleum ether and subjected to alumina column chromatography by eluting with a mixture of petroleum ether and ethyl ether. The solvent was distilled away from the eluate containing Coenzyme $Q_{10}$. The residual oil was dissolved in a small amount of ethyl alcohol and allowed to stand in a refrigerator whereby crystals of Coenzyme $Q_{10}$ appeared. These crystals were recrystalyzed from ethyl alcohol three times and 85.8 milligrams of crystals of Coenzyme $Q_{10}$ were obtained.

On the other hand, the same cultivation as above was conducted by use of 15 liters of the culture medium to which no isopentenyl alcohol was added. In the same manner as above, 1090 grams of wet cells (132 grams as dry cells) were obtained. Further the same procedure as above was applied whereby 48.7 milligrams of crystals of Coenzyme $Q_{10}$ were obtained.

Based upon the above data, the effect of isopentenyl alcohol on the production of Coenzyme $Q_{10}$ was calculated. The addition of isopentenyl alcohol to the culture broth increased the yield of Coenzyme $Q_{10}$ per liter of the broth by approximately 76%, and by approximately 62% per gram of dry cells. Thus it was clearly confirmed that the addition of isopentenyl alcohol was effective to increase the yield of Coenzyme $Q_{10}$.

EXAMPLE 2

*Rhodotorula glutinis* FERM-P4835 was cultivated in the same medium and in the same manner as described in Example 1, and 1240 grams of wet cells (155 grams as dry cells) were obtained. The wet cells were treated in the same manner as Example 1 and 54.7 milligrams of crystals of Coenzyme $Q_{10}$ were obtained. On the other hand, the same microorganism was cultivated in the same medium as above except that no isopentenyl alcohol was added, and 1200 grams of wet cells (149 grams as dry cells) were obtained. From the cells, 32.8 milligrams of crystals of Coenzyme $Q_{10}$ were obtained.

Based upon the above data, the effect of isopentenyl alcohol on the production of Coenzyme $Q_{10}$ was compared. The addition of isopentenyl alcohol to the culture medium increased the yield of Coenzyme $Q_{10}$ per liter of the broth by approximately 67% and by approximately 60% per gram of the dry cells.

EXAMPLE 3

*Sporobolomyces salmonicolor* FERM-P4836 was cultivated in the same medium and in the same manner as described in Example 1, and 940 grams of wet cells (118 grams as dry cells) were obtained. The wet cells were treated in the same way as in Example 1 and 61.6 milligrams of crystals of Coenzyme $Q_{10}$ were obtained. On the other hand, the same microorganism was cultivated by use of the culture medium to which no isopentenyl alcohol was added, and 990 grams of wet cells (124 grams as dry cells) were obtained. From the cells, 43.4 milligrams of crystals of Coenzyme $Q_{10}$ were obtained.

Based upon the above data, the effect of isopentenyl alcohol on the production of Coenzyme $Q_{10}$ was compared. The addition of isopentenyl alcohol to the culture medium increased the yield of Coenzyme $Q_{10}$ per liter of the broth by approximately 42%, and by approximately 49% per gram of the dry cells.

EXAMPLE 4

*Torulopsis aeria* FERM-P4837 was cultivated in the same medium and in the same manner as described in Example 1, and 765 grams of wet cells (96 grams as dry cells) were obtained. These were treated in the same way as Example 1, and 38.9 milligrams of crystals of Coenzyme $Q_{10}$ were obtained. On the other hand, the same microorganism was cultivated in the same medium as above except that no isopentenyl alcohol was added, and 790 grams of wet cells (99 grams as dry cells) were obtained. From the cells, 31.6 milligrams of crystals of Coenzyme $Q_{10}$ were obtained.

Based upon the above data, the effect of isopentenyl alcohol on the production of Coenzyme $Q_{10}$ was compared. The addition of isopentenyl alcohol to the culture medium increased the yield of Coenzyme $Q_{10}$ per liter of the broth by approximately 23%, and by approximately 27% per gram of the dry cells.

EXAMPLE 5

Sporidiobolus jonsonii IFO-6903 was cultivated by the same procedure as in Example 1 and 1110 grams of wet cells (155 grams as dry cells) were obtained. These were treated in the same way as Example 1 and 74.4 milligrams of crystals of Coenzyme $Q_{10}$ were obtained. On the other hand, the same microorganism was cultivated in the same medium as above except that no isopentenyl alcohol was added, and 1050 grams of wet cells (142 grams as dry cells) were obtained. From the cells 55.4 milligrams of crystals of Coenzyme $Q_{10}$ were obtained.

Based upon the above data, the effect of isopentenyl alcohol on the production of Coenzyme $Q_{10}$ was compared. The addition of isopentenyl alcohol to the culture medium increased the yield of Coenzyme $Q_{10}$ per liter of the broth by approximately 34% and by approximately 23% per gram of the dry cells.

EXAMPLE 6

Oosporidium margaritiferum ATCC-10676 was cultivated by the same procedure as in Example 1, and 1540 grams of wet cells (260 grams as dry cells) were obtained. These were treated in the same way as Example 1 and 78.8 milligrams of crystals of Coenzyme $Q_{10}$ were obtained. On the other hand, the same microorganism was cultivated in the same medium as above except that no isopentenyl alcohol was added, and 1490 grams of wet cells (240 grams as dry cells) were obtained. From the cells 54.2 milligrams of crystals of Coenzyme $Q_{10}$ were obtained.

Based upon the above data, the effect of isopentenyl alcohol on the production of Coenzyme $Q_{10}$ was compared. The addition of isopentenyl alcohol to the culture medium increased the yield of Coenzyme $Q_{10}$ per liter of the broth by approximately 45% and by approximately 34% per gram of dry cells.

EXAMPLE 7

In a 30 liter-jar fermentor was placed 15 liters of culture medium (pH 5.5) containing 0.5% of $KH_2PO_4$, 0.1% of $MgSO_4.7H_2O$, 3% of glucose, 0.1% of $(NH_4)_2SO_4$, 0.5% of corn steep liquor and 0.1% of malt extract. After sterilized with steam, 645 milligrams of isopentenyl alcohol dissolved in 10 milliliters of ethyl alcohol was added. Aspergillus fumigatus FERM-P4838, which had been previously cultured in 500 milliliters of the medium having the same composition as described above for 36 hours, was inoculated in the above culture medium and cultivated for 72 hours at 27° C. with aeration of 15 liters per minutes under condition of stirring 300 r.p.m. Against the variation of pH of the culture medium, aqueous ammonium or aqueous hydrochloric acid was added to maintain pH 5.5.

After the cultivation, the culture was filtered whereby 1330 grams of wet cells (140 grams as dry cells) were obtained. The wet cells were subjected to the same procedure as in Example 1, and 47.8 milligrams of Coenzyme $Q_{10}$ were obtained. On the other hand, the same strain was cultivated by use of 15 liters of the culture medium to which no isopentenyl alcohol was added, and 1430 grams of wet cells (145 grams as dry cells) were obtained. From the cells 29.3 milligrams of crystals of Coenzyme $Q_{10}$ were obtained.

Based upon the above data, the effect of isopentenyl alcohol on the production of Coenzyme $Q_{10}$ was calculated. The addition of isopentenyl alcohol to the culture broth increased the yield of Coenzyme $Q_{10}$ per liter of the broth by approximately 64%, and by approximately 69% per gram of the dry cells. Thus it was clearly confirmed that the addition of isopentenyl alcohol to the culture medium was effective to increase the yield of Coenzyme $Q_{10}$.

EXAMPLE 8 Cladosporium fulvum FERM-P4839 was cultivated by the same procedure as in Example 7, and 1210 grams of wet cells (132 grams as dry cells) were obtained. These were treated in the same way as Example 1, and 62.5 milligrams of crystals of Coenzyme $Q_{10}$ were obtained. On the other hand, the same microorganism was cultivated in the same medium as above except that no isopentenyl alcohol was added, and 1150 grams of wet cells (127 grams as dry cells) were obtained. From the cells 47.5 milligrams of crystals of Coenzyme $Q_{10}$ were obtained.

Based upon the above data, the effect of isopentenyl alcohol on the production of Coenzyme $Q_{10}$ was compared. The addition of isopentenyl alcohol to the culture medium increased the yield of Coenzyme $Q_{10}$ per liter of the broth by approximately 32%, and by approximately 27% per gram of dry cells.

Thus it was clearly confirmed that the addition of isopentenyl alcohol was effective to increase the yield of Coenzyme $Q_{10}$.

What is claimed is:

1. In the process for producing Coenzyme $Q_{10}$, which comprises cultivating a microorganism belonging to genus Cryptococcus, Rhodotorula, Sporobolomyces, Torulopsis, Sporidiobolus, Oosporidium, Aspergillus and Cladosporium, capable of producing Coenzyme $Q_{10}$, in a culture medium to produce Coenzyme $Q_{10}$ and recovering Coenzyme $Q_{10}$ from said culture medium, the improvement comprising admixing isopentenyl alcohol with said culture medium whereby the yield of Coenzyme $Q_{10}$ is increased.

2. The process of claim 1, wherein the microorganism is selected from the group consisting of Cryptococcus laurentii FERM-P4834, Rhodotorula glutinis FERM-P4835, Sporobolomyces salmonicolor FERM-P4836, Torulopsis aeria FERM-P4837, Sporidiobolus jonsonii IFO-6903, Oosporidium margaritiferum ATCC-10676, Aspergillus fumigatus FERM-P4838, and Cladosporium fulvum FERM-P4839.

3. The process of claim 1 wherein the concentration of isopentenyl alcohol in said culture medium is from $1 \times 10^{-5}$ to $5 \times 10^{-3}$ mole per liter.

4. The process of claim 2 wherein the concentration of isopentenyl alcohol in said culture medium is from $5 \times 10^{-5}$ to $5 \times 10^{-4}$ mole per liter.

5. The process of claim 1 or claim 4 wherein said Coenzyme $Q_{10}$ is cultivated by agitation with aeration with a culture medium at a pH of from 4 to 7 and at a temperature of from 25° to 35° C.

6. The process of claim 5 wherein said microorganism is *Cryptococcus laurentii* FERM-P4834.

7. The process of claim 5 wherein said microorganism is *Rhodotorula glutinis* FERM-P4835.

8. The process of claim 5 wherein said microorganism is *Sporobolomyces salmonicolor* FERM-P4836.

9. The process of claim 5 wherein said microorganism is *Torulopsis aeria* FERM-P4837.

10. The process of claim 5 wherein said microorganism is *Sporidiobolus jonsonii* IFO-6903.

11. The process of claim 5 wherein said microorganism is *Oosporidium margaritiferum* ATCC-10676.

12. The process of claim 5 wherein said microorganism is *Aspergillus fumigatus* FERM-P4838.

13. The process of claim 5 wherein said microorganism is *Cladosporium fulvum* FERM-P4839.

* * * * *